(12) United States Patent
Blumenkranz (10) Patent No.: US 8,945,174 B2
(45) Date of Patent: Feb. 3, 2015

(54) MEDICAL INSTRUMENT WITH FLEXIBLE JAW MECHANISM

(75) Inventor: Stephen J. Blumenkranz, Redwood City, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 195 days.

(21) Appl. No.: 13/210,142

(22) Filed: Aug. 15, 2011

(65) Prior Publication Data
US 2013/0046336 A1    Feb. 21, 2013

(51) Int. Cl.
A61B 17/00 (2006.01)
A61B 17/29 (2006.01)
A61B 17/28 (2006.01)
A61B 19/00 (2006.01)

(52) U.S. Cl.
CPC ......... A61B 17/29 (2013.01); *A61B 2017/2825* (2013.01); *A61B 2019/2234* (2013.01); *A61B 2017/00867* (2013.01); *A61B 2017/2926* (2013.01); *A61B 2017/2937* (2013.01); *A61B 2017/2939* (2013.01)
USPC ........... 606/205; 606/206; 606/207; 606/174; 606/51

(58) Field of Classification Search
CPC ........... A61B 17/29; A61B 2017/2825; A61B 2017/2939; A61B 2017/2926; A61B 2017/2937; A61B 2017/00867; A61B 2019/2234
USPC ........ 606/205, 206, 207, 174, 51, 52, 83, 170
See application file for complete search history.

(56) References Cited

U.S. PATENT DOCUMENTS

| | | | |
|---|---|---|---|
| 2,818,636 A | 1/1958 | Fentress et al. | |
| 4,165,745 A | 8/1979 | Heifetz | |
| 4,610,475 A | 9/1986 | Heiserman | |
| 5,052,402 A * | 10/1991 | Bencini et al. | 600/564 |
| 5,318,589 A | 6/1994 | Lichtman | |
| 5,325,845 A | 7/1994 | Adair | |
| 5,373,854 A | 12/1994 | Kolozsi | |
| 5,395,375 A | 3/1995 | Turkel et al. | |
| 5,476,479 A | 12/1995 | Green et al. | |
| 5,496,317 A | 3/1996 | Goble et al. | |
| 5,527,339 A | 6/1996 | Koscher et al. | |
| 5,575,805 A * | 11/1996 | Li | 606/206 |
| 5,906,630 A | 5/1999 | Anderhub et al. | |
| 5,916,146 A | 6/1999 | Allotta et al. | |
| 5,968,074 A | 10/1999 | Prestel | |

(Continued)

FOREIGN PATENT DOCUMENTS

WO    WO-2013025831 A2    2/2013

OTHER PUBLICATIONS

Abani et al., "Minimally Invasive Surgical Tools", Precision Systems Design Laboratory, Mechanical Engineering, Publisher: University of Michigan, downloaded Apr. 6, 2011, 1 page, Published in: Michigan, US.

(Continued)

*Primary Examiner* — Tuan V Nguyen
*Assistant Examiner* — Tin Nguyen (57) ABSTRACT

A medical instrument includes a unitary jaw structure having: a connector portion, a first jaw portion flexibly integral with the connector portion, a first arm portion integral with the first jaw portion, and an actuator portion flexibly integral with the first arm portion for causing rotating motion of the first jaw portion upon linear motion of the actuator portion.

23 Claims, 5 Drawing Sheets

(56) References Cited

U.S. PATENT DOCUMENTS

| | | | |
|---|---|---|---|
| 6,214,010 | B1 | 4/2001 | Farley et al. |
| 6,368,290 | B1 * | 4/2002 | Baska .......................... 600/564 |
| 6,491,626 | B1 | 12/2002 | Stone et al. |
| 6,623,482 | B2 | 9/2003 | Pendekanti et al. |
| 6,817,974 | B2 | 11/2004 | Cooper et al. |
| 6,843,793 | B2 | 1/2005 | Brock et al. |
| 6,949,106 | B2 | 9/2005 | Brock et al. |
| 7,090,683 | B2 | 8/2006 | Brock et al. |
| 7,147,650 | B2 | 12/2006 | Lee |
| 7,169,141 | B2 | 1/2007 | Brock et al. |
| 7,214,230 | B2 | 5/2007 | Brock et al. |
| 7,320,700 | B2 | 1/2008 | Cooper et al. |
| 7,338,513 | B2 | 3/2008 | Lee et al. |
| 7,371,210 | B2 | 5/2008 | Brock et al. |
| 7,608,083 | B2 | 10/2009 | Lee et al. |
| 7,682,307 | B2 | 3/2010 | Danitz et al. |
| 7,785,252 | B2 | 8/2010 | Danitz et al. |
| 2004/0260198 | A1 | 12/2004 | Rothberg et al. |
| 2005/0090809 | A1 | 4/2005 | Cooper et al. |
| 2005/0119527 | A1 | 6/2005 | Banik et al. |
| 2005/0216033 | A1 * | 9/2005 | Lee et al. ....................... 606/130 |
| 2005/0273085 | A1 | 12/2005 | Hinman et al. |
| 2006/0184198 | A1 * | 8/2006 | Bales et al. ................... 606/205 |
| 2009/0131975 | A1 * | 5/2009 | Ahlberg et al. ............... 606/206 |
| 2009/0198272 | A1 | 8/2009 | Kerver et al. |
| 2009/0209960 | A1 | 8/2009 | Chojin |
| 2010/0004663 | A1 | 1/2010 | Murphy et al. |
| 2010/0030238 | A1 | 2/2010 | Viola et al. |
| 2010/0032581 | A1 | 2/2010 | Grosse et al. |
| 2010/0160940 | A1 | 6/2010 | Lutze et al. |
| 2010/0234831 | A1 | 9/2010 | Hinman et al. |
| 2010/0331856 | A1 | 12/2010 | Carlson et al. |
| 2013/0046317 | A1 | 2/2013 | Blumenkranz |

OTHER PUBLICATIONS

Bhisitkul et al., "Development of Microelectromechanical Systems (MEMS) forceps for intraocular surgery", "Br J. Ophthalmol 2005", Aug. 2005, pp. 1586-1588, No. 89, Published in: San Francisco, US.

Birglen et al., "Force Analysis of Connected Differential Mechanisms: Application to Grasping", "International Journal of Robotics Research", Oct. 2006, pp. 1033-1046, Publisher: Sage Publications, Published in: Quebec, CA.

Kota et al., "Design and Application of Compliant Mechanisms for Surgical Tools", "Journal of Biomechanical Engineering", Nov. 2005, pp. 981-989, vol. 127, Publisher: ASME, Published in: Michigan, US.

Mertmann et al., "Grippers for the Micro Assembly Containing Shape Memory Actuators and Sensors", "Journal De Physique IV", Nov. 1997, pp. C5-621-626, vol. 7, Publisher: Institut fuer Werstoffe, Ruhr-Universitaet, Published in: Bochum, Germany.

Zubir et al., "Development of a novel flexure based microgripper for precision manipulation of micro-objects", "Robotics and Mechatronics Research Laboratory", Downloaded on May 23, 2010 at 19:43:13 UTC from IEEE Xplore, 6 pages, Publisher: Monash University, Published in: Victoria, Australia.

Abani, Rosa and Tristan Trutna, "Minimally Invasive Surgical Tools," Research from Precision Systems Design Laboratory, Mechanical Engineering, University of Michigan, 2010, 1 page, Internet: http://awtarlab3.engin.umich.edu/research.php.

Bhisitkul, R.B. and C.G. Keller, "Development of Microelectromechanical Systems (MEMS) Forceps for Intraocular Surgery," Scientific Report, British Journal of Ophthalmology, 2005, vol. 89, Issue 1, pp. 1586-1588.

Birglen, Lionel and Clément M. Gosselin, "Force Analysis of Connected Differential Mechanisms: Application to Grasping," The International Journal of Robotics Research, Oct. 2006, vol. 25, No. 10, pp. 1033-1046, Sage Publications.

Doria, Mario and Lionel Birglen, "Design of an Underactuated Compliant Gripper for Surgery Using Nitinol," Journal of Medical Devices, Mar. 2009, vol. 3, Issue 1, Abstract, p. 011007, ASME.

Kota S. et al., "Design and Application of Compliant Mechanisms for Surgical Tools," Technical Briefs, Journal of Biomechanical Engineering, Nov. 2005, vol. 127, pp. 981-989, ASME.

Mertmann, M. and E. Hornbogen, "Grippers for the Micro Assembly Containing Shape Memory Actuators and Sensors," Le Journal de Physique IV France 7 (1997), Conference C5, Supplement of Journal de Physique III of Nov. 1997, pp. C5-621-C5-626.

Ramu, G. and G.K. Ananthasuresh, "A Flexure-based Deployable Stereo Vision Mechanism and Temperature and Force Sensors for Laparoscopic Tools," 14th National Conference on Machines and Mechanisms (NaCoMM09), Durgapur, India, Dec. 17-18, 2009, NaCoMM-2009-BMGR2, pp. 440-445.

Zubir, Mohd N.M. and Bijan Shirinzadeh, "Development of a novel flexure based microgripper for precision manipulation of micro-objects," IEEE International Conference on Industrial Technology (ICIT 2009), 2009, pp. 1-6.

Beasley, Ryan A. and Robert D. Howe, "Model-based error correction for flexible robotic surgical instruments," Proceedings of Robotics: Science and Systems Conference, 2005, pp. 359-364.

Choi, David Y. and Cameron N. Riviere, "Flexure-Based Manipulator for Active Handheld Microsurgical Instrument," Proceedings of the 2005 IEEE 27th Annual Conference on Engineering in Medicine and Biology, Shanghai, China, Sep. 1-4, 2005, pp. 5085-5088, IEEE.

International Search Report and Written Opinion for Application No. PCT/US2012/050988, mailed on Feb. 20, 2013, 12 pages.

Sahai, Ranjana et al., "Semi-Automated Micro Assembly for Rapid Prototyping of a One DOF Surgical Wrist," International Conference on Intelligent Robots and Systems (IROS 2003), Las Vegas, NV, Oct. 27-31, 2003, vol. 2, pp. 1882-1888, IEEE.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Choi, David Y. and Cameron N. Riviere, "Flexure-Based Manipulator for Active Handheld Microsurgical Instrument,"Proceedings of the 2005 IEEE 27th Annual Conference on Engineering in Medicine and Biology, Shanghai, China, Sep. 1-4, 2005, pp. 5085-5088, IEEE.

* cited by examiner

MEDICAL INSTRUMENT WITH FLEXIBLE JAW MECHANISM

TECHNICAL FIELD

The present invention relates generally to a medical instrument, and more particularly to a medical instrument with jaws.

BACKGROUND ART

Modern tools and manipulating instruments, especially instruments with jaws for performing surgical operations, such as cutting, grasping and holding, are providing increasing levels of functionality and strength to support modern needs including applications in minimally invasive and micro-surgery.

Often, the tools available are not efficient in applying the correct amount of force precisely or being precisely positioned. As surgical instruments decrease in size, a number of problems occur with mechanisms having jaws, such as forceps, graspers, and scissors.

New surgical techniques have created less invasive procedures, such as minimally invasive surgery (MIS) and robotic MIS, which has created the need for smaller diameter instruments. The need for small instruments is motivated by patient concern for cosmetic healing with minimal or no scars and less incision size related post-operative pain.

The development of less invasive medical instruments is also motivated by surgeons who need smaller instruments to address smaller anatomy such as small blood vessel and nerve re-anastomosis, ophthalmic surgery, vasectomy reversal and the like. Another surgeon motivation for developing less invasive medical instruments and procedures is the desire to make patients happy with less noticeable scarring, less post-operative pain and more rapid healing.

One of the technical obstacles to producing these less invasive medical instruments is the transmission of force from the mechanical actuator to the instrument jaw or end effector on the other end. The delivery of too much force or too little can present a surgeon with additional unwanted complications in surgery.

Another difficulty is the precise positioning and movement of the medical instrument jaws or end effector. Providing a precise control through a system of linkages can be difficult. The combined linkages have inherent movement error called "hysteresis", which is usefully thought of as lost motion or wasted energy. The hysteresis of a medical instrument is caused by the friction between moving parts, and the stretching of interconnecting parts.

Block and tackle style mechanisms for jaw actuation can provide greater mechanical advantage to the actuating cable but add to parts count, assembly cost, and mechanism friction.

The need to reduce costs, to improve efficiencies and performance, and to meet competitive pressures adds an even greater urgency to the critical necessity for finding answers to these problems. Solutions to these problems have been long sought but prior developments have not taught or suggested any solutions and, thus, solutions to these problems have long eluded those skilled in the art.

DISCLOSURE OF THE INVENTION

The present invention provides a medical instrument that includes: a unitary jaw structure having a connector portion, a first jaw portion flexibly integral with the connector portion, a first arm portion integral with the first jaw portion, and an actuator portion flexibly integral with the first arm portion for causing rotating motion of the first jaw portion upon linear motion of the actuator portion.

Certain embodiments of the invention have other steps or elements in addition to or in place of those mentioned above. The steps or elements will become apparent to those skilled in the art from a reading of the following detailed description when taken with reference to the accompanying drawings.

BEST MODE FOR CARRYING OUT THE INVENTION

The following embodiments are described in sufficient detail to enable those skilled in the art to make and use the invention. It is to be understood that other embodiments would be evident based on the present disclosure, and that system, process, or mechanical changes may be made without departing from the scope of the present invention.

In the following description, numerous specific details are given to provide a thorough understanding of the invention. However, it will be apparent that the invention may be practiced without these specific details. In order to avoid obscuring the present invention, some well-known devices, instrument configurations, and process steps are not disclosed in detail.

For expository purposes, the term "horizontal" as used herein is defined as the horizontal direction seen when viewing the drawing as indicated by the figure designation of "FIG.". The term "vertical" refers to a direction perpendicular to the horizontal as just defined. Terms, such as "above", "below", "bottom", "top", "side" (as in "sidewall"), "higher", "lower", "upper", "over", and "under", are defined with respect to the horizontal, as shown in the figures. The term "on" means there is direct contact between the elements described. Generally, the invention can be operated in any orientation.

Also, in the following description, connected and coupled are used to describe a relationship between two members. The term "connected" means that the two members are physically and directly joined to each other.

Different members can be connected in variety of ways. For example, different members can be connected by being formed adjacent to each other, such as through molding or carving. Also, for example, different members can be connected by being attached together, such as through adhesives, fasteners, welds, or brazing.

The term "coupled" means that the two members are physically linked through one or more other members. The phrases "reciprocating motion" and "reciprocating movement" are defined to describe a repetitive up-and-down or back-and-forth linear or angular rotational motion. The phrases "distal" and "proximal" are defined to respectively indicate the directions designated by the related arrows in FIG. 1 or along the path of connectivity between the point where the instrument couples to the robot arm (proximal) and the instrument tip that contacts surgical patient tissue (distal).

The drawings showing embodiments of the system are semi-diagrammatic and not to scale and, particularly, some of the dimensions are for the clarity of presentation and are shown exaggerated in the drawing FIGs. Similarly, although the views in the drawings for ease of description generally show similar orientations, this depiction in the FIGs. is arbitrary for the most part. Generally, the invention can be operated in any orientation.

Often, the surgical instruments available are not efficient in applying the correct amount of jaw grip force or positioning the jaws precisely. As surgical instruments decrease in size, a number of problems occur with mechanisms having jaws, such as forceps, graspers, and scissors.

As the ratio of jaw length to jaw actuating lever length increases, the mechanical advantage of an actuating system decreases. Therefore, for a desired jaw closure force, most actuating system cables and pulleys require a relatively greater force to be exerted by the actuating cable as surgical instrument diameter decreases.

In jaw systems using pins or shafts on which the individual jaws pivot, the greater cable force increases the pivot pin friction resisting jaw rotation. This means greater actuating force than desired must be applied for jaw actuation.

The higher cable force also requires a corresponding increase in cross-sectional shear area of the pivot pin supporting the jaws thus requiring a larger pivot pin diameter to prevent failures. The ratio of actuator pulley diameter to pivot pin diameter decreases as a result of the decrease in pulley size and increase in pin size, which further increases the frictional torque resisting jaw rotation and further increases the actuating cable force to achieve a given jaw force.

The higher frictional forces and lower mechanical advantage increase cable axial deflection or stretch so that greater movement than desired of the proximal end of the actuating cable is required for a predetermined amount of jaw rotation and force, which means the effective drive train compliance is increased.

Since the hysteresis of any mechanism varies with the product of the mechanism friction multiplied by its drive train compliance, the combined effect of these friction and compliance increases is a large increase in hysteresis as the cross-sectional diameter of an instrument, such as a gripper, decreases for a given type of jaw mechanism. This is particularly detrimental when there is rubbing friction with higher starting friction that results in uneven or unpredictable motion effects sometimes called stiction or stick-slip.

Therefore, in order to enable smaller smoothly functioning surgical instruments, it is desirable to have a new jaw mechanism with lower friction, greater jaw lever mechanical advantage, and lower effective drive train compliance.

Others have addressed these problems by providing heavy solid actuating rods with higher axial stiffness (lower compliance). However, large solid jaw actuating rods interfere with the flexibility or prevent the use of an articulated wrist used to position and orient the jaws and also may be susceptible to bending stress fatigue failure in high cycle life uses. Thus heavy solid rod actuating members are best adapted to manual laparoscopic surgical instruments without a wrist and poorly adapted to robotic laparoscopic surgical instruments with an articulated wrist.

Figure 1:
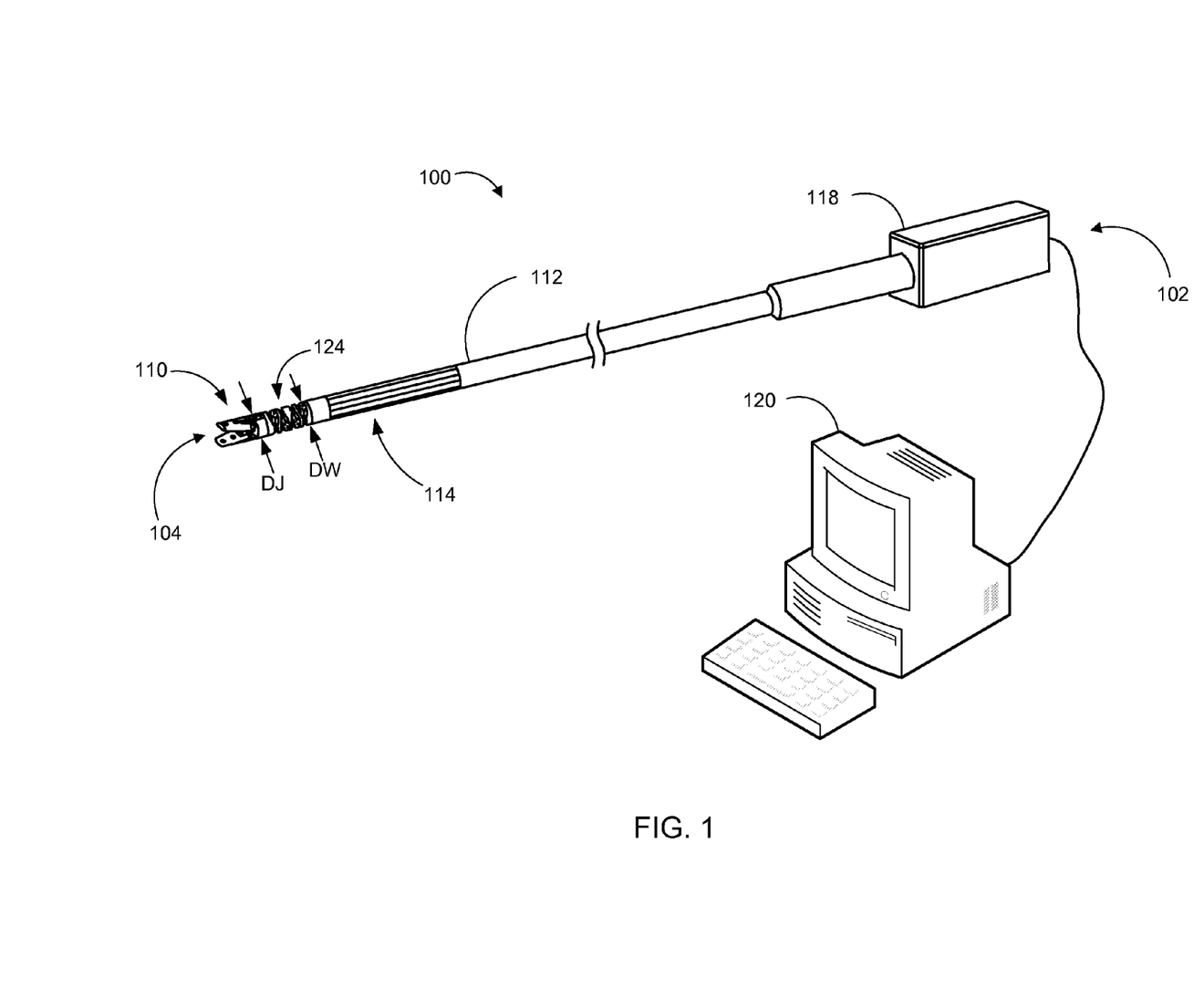
FIG. 1 is a medical instrument with a unitary jaw structure in an embodiment of the present invention.

Referring now to FIG. 1, therein is shown a medical instrument 100 with a unitary jaw structure 110 in an embodiment of the present invention. The medical instrument 100 has a proximal end 102 and a distal end 104.

The medical instrument 100 can include the unitary jaw structure 110 at the distal end 104, a tube 112 with actuating members 114, and an actuator system 118 at the proximal end 102. The unitary jaw structure 110 in an embodiment of the present invention is analogous to a human hand. The term "unitary" means a structure of a single unit of material. The unitary jaw structure 110 can be manufactured from a single material as a single unit.

The medical instrument 100 can include a wrist mechanism 124, analogous to a human wrist, attached to or integrally formed with the unitary jaw structure 110. The wrist mechanism 124 can be connected to the unitary jaw structure 110 using an adhesive or a mechanical fastener or it may also be welded or brazed. In an alternative embodiment, the unitary jaw structure 110 and the wrist mechanism 124 can together be manufactured from a single material as a single unit.

The unitary jaw structure 110 can be carved or shaped out of a single unit of material, such as plastic or metal alloy. For examples, the unitary jaw structure 110 can be formed by cutting and carving polypropylene plastic or metal alloy or can be formed by using wire electrical discharge machining (EDM) process and post treatment to remove surface layer re-melt, such as when used to shape Nitinol alloy.

The unitary jaw structure 110 can also be molded into shape. For example, the unitary jaw structure 110 can be molded plastic or cast metal. The unitary jaw structure 110 also can be formed as a single injection molding of a polymer, such as fiber reinforced polyether ether ketone (PEEK), or by metal injection molding (MIM) into a die or mold that has a continuous cavity.

The unitary jaw structure 110 is shown having a cylindrical configuration with a taper narrowing towards the distal end 104. The taper allows the unitary jaw structure 110 to project into tight spaces and move between obstacles such as organs or blood vessels.

The unitary jaw structure 110 provides for improved manufacturing operations with the advantage of eliminating assembly operations because of its one piece structure. Because of reduced cost, it is feasible to make the unitary jaw structure 110 for single use applications. A single use tool avoids the need for the handling and processing associated with cleaning and resterilization after use, as well as the need for certain instrument design requirements for resterilization, such as the ability to withstand autoclaving.

The tube 112 holds the unitary jaw structure 110 at a location in space. For example, the tube 112 can be straight tube of a medical instrument.

For illustrative purposes the tube 112 is shown as a hollow cylindrical member encasing the actuating members 114 within the tube 112. However, it is understood that the tube 112 can be different and have various cross-sectional shapes, or be solid and have external versions of the actuating members 114.

The unitary jaw structure 110 is attached at the distal end 104 of the tube 112 and the actuator system 118 at the proximal end 102. Generally, the unitary jaw structure 110 is the more distal portion and the wrist mechanism 124 is the more proximal portion.

The wrist mechanism 124 is a member that bends or provides multi-axis movement to change the relative position and orientation of the unitary jaw structure 110. For example, the wrist mechanism 124 can be a ball and socket or may have more than one pin jointed hinges at right angles to each other.

Also, for example, the wrist mechanism 124 can be a flexible mechanism manufactured from a single material as a single unit that can move to allow for the medical instrument 100 to position the unitary jaw structure 110. The wrist mechanism 124 can be a flexible member that can bend without discrete pivoting pin joints. The wrist mechanism 124 is supported by the tube 112.

In one embodiment, the unitary jaw structure 110 has a diameter, depicted as DJ, and the wrist mechanism 124 has a diameter DW, as depicted in FIG. 1. In one embodiment, DW is equal to DJ so that both portions of the unitary jaw structure 110 can enter easily through the same cannula in an incision during a minimally invasive surgical procedure.

The actuator system 118 exerts forces coupled by the actuating members 114 to bend the wrist mechanism 124 and to actuate the unitary jaw structure 110. The actuating members 114, for example, can be a rod, cable, or cable and pulley system that is pushed or pulled to bend the wrist mechanism 124 along the direction of applied force. The actuator system 118 can also be coupled through the actuating members 114 to convey the forces to cause rotating reciprocation motion of the unitary jaw structure 110.

The actuator system 118 may include or may be coupled to electrical, hydraulic, or pneumatic power systems to generate the applied forces. A control system 120 can be coupled to the actuator system 118 for controlling the amount of applied forces and motion for the unitary jaw structure 110 and the wrist mechanism 124. The control system 120 is a mechanism that can control the operation of the unitary jaw structure 110. For example, the control system 120 can be a computer and motor assembly or an assembly of handles, gears, and levers.

Figure 2:
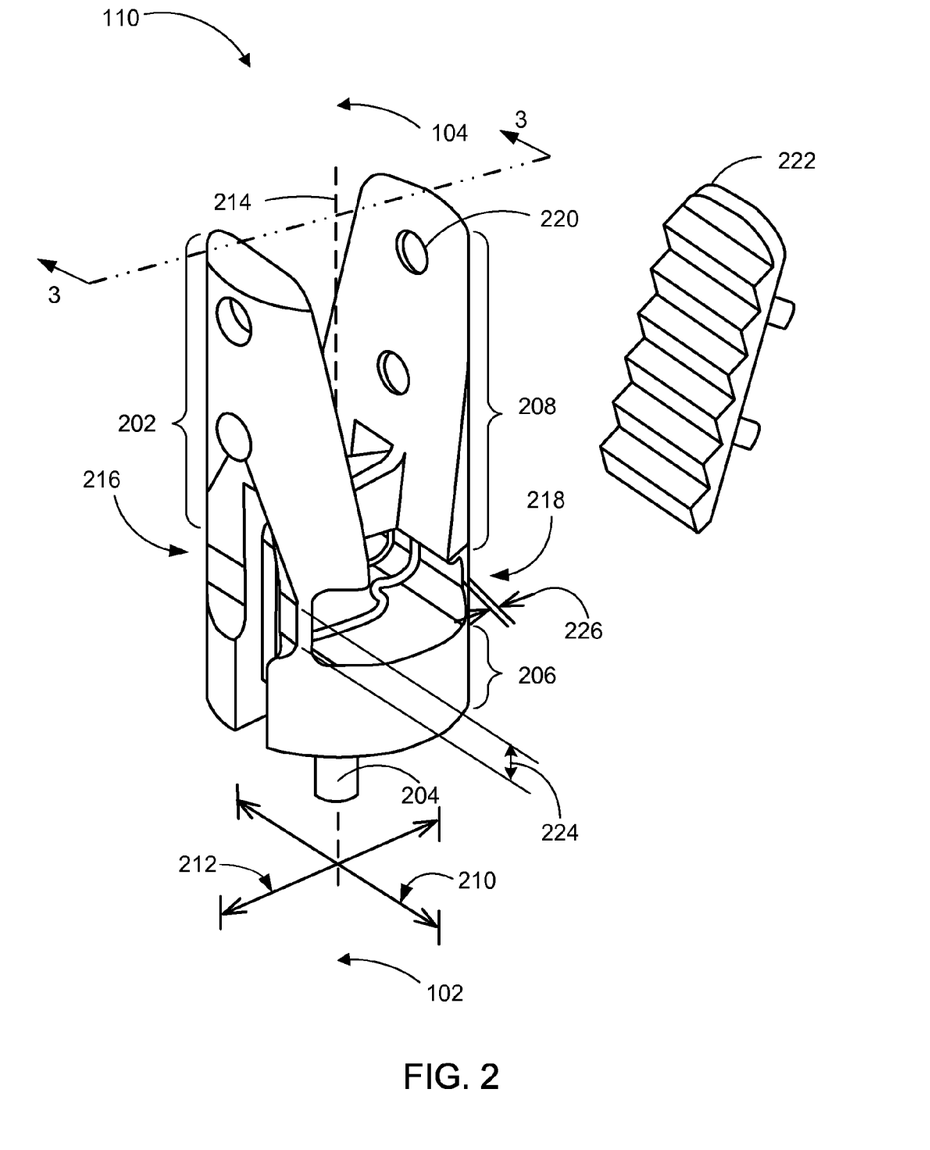
FIG. 2 is an enlarged detailed isometric view of the unitary jaw structure.

Referring now to FIG. 2, therein is shown an enlarged detailed isometric view of the unitary jaw structure 110. The unitary jaw structure 110 includes a first jaw portion 202, an actuator portion 204, a connector portion 206, and a second jaw portion 208.

The unitary jaw structure 110 has a first transverse dimension 210 and a second transverse dimension 212 along a plane orthogonal to a center line 214. The first transverse dimension 210 and the second transverse dimension 212 are shown to be the same but do not need to be and may be adjusted based on the geometry of the unitary jaw structure 110. In the case in which they are equal, the unitary jaw structure 110 may be circular in cross section as illustrated in FIG. 2.

The first jaw portion 202 is a portion of the unitary jaw structure 110 that is radially symmetric to the second jaw portion 208. The first jaw portion 202, the second jaw portion 208, or a combination thereof can be used to grab, manipulate, cut, or perform a combination of operations. The first jaw portion 202 and the second jaw portion 208 can rotate equal distances in opposite direction simultaneously along arcs centered on respectively a first flexible hinge 216 and a second flexible hinge 218.

The first jaw portion 202 can extend away from the connector portion 206. The first jaw portion 202 can have a variety of shapes. For example, the first jaw portion 202 can be trapezoidal, rectangular, or oval in shape extending away from the connector portion. Also, for example, the first jaw portion 202 can have a planar outer surface or a rounded outer surface.

The first flexible hinge 216 and the second flexible hinge 218 are flexible members, also known as flexures, that couple two other relatively rigid members. For example, the first flexible hinge 216 can couple the first jaw portion 202 and the connector portion 206. Also, for example, the second flexible hinge 218 can couple the second jaw portion 208 and the connector portion 206.

The first flexible hinge 216 and the second flexible hinge 218 can have a hinge length 224 and a hinge thickness 226. The hinge length 224 can be the length of the first flexible hinge 216 and the second flexible hinge 218, which can be measured in a direction parallel to the center line 214. The hinge thickness 226 can be the thickness of the first flexible hinge 216 and the second flexible hinge 218, which can be measured in a direction parallel to the second transverse dimension 212.

The hinge thickness 226 can be sufficiently less than the hinge length 224 that it provides a bending compliance between the coupled rigid members allowing one rigid member to rotate with respect to the other about an axis perpendicular to the hinge length 224 and the hinge thickness 226. The axis for rotation can be located at the midpoint of the hinge length 224 and the hinge thickness 226 when the flexure is straight.

The hinge length 224 and the hinge thickness 226 can have a ratio of length to thickness such that the bending strain and the resulting stress in the flexure are within limits based on its material properties, such as yield strength or fatigue strength limit, angular range of motion, and required flexing motion cycles. The first flexible hinge 216 and the second flexible hinge 218 may rigidly transmit forces along at least the hinge length 224 between the two coupled members. Advantageously, when moving, the first flexible hinge 216 and the second flexible hinge 218 have only low internal hysteresis losses in the material, also called equivalent friction, which are significantly lower than the corresponding actual friction losses in a similarly loaded pin jointed hinge. Hysteresis loss is the loss in motion or energy in mechanisms and structures due to the physical property thereof The first flexible hinge 216 and the second flexible hinge 218 can be a compact flexure hinge. A compact flexure hinge is a flexure made from a plastic material preferably such as injection molded polypropylene or ultra-high molecular weight polyethylene (UHMW-PE) whose material properties permit a short flexure length while at the same time permitting a high number of flexing motion cycles. For example, the flexure length can be less than twice the hinge thickness 226 or equivalent thickness, such as the thickness at the vertex point when the hinge has a concave shape. The compact flexure hinge can be bounded by concave curved surfaces.

The flex life of a compact flexure hinge, the number of times a compact flexure hinge can be reliably flexed or bent, can be enhanced by providing that the melted plastic flows through the hinge from one coupled rigid member toward the other as the mold fills and by flexing the hinge fully in both directions immediately upon removal from the mold.

Also advantageously, the compact flexure hinge may reduce cost by eliminating multiple separate components and associated assembly labor as well as by using a low cost material. The compact flexure hinge benefits the rigidity of the jaw hinge in the direction of the flexure thickness. Separately important here is the flexure design of the combined jaw mechanism. The compact flexure hinge embodiment should be covered too.

Because of their reduced length in relation its thickness, the first flexible hinge 216 and the second flexible hinge 218 when configured as the compact flexure hinges, advantageously provide relatively greater stiffness than conventional elongated flexures with respect to forces between the coupled members in the direction of the hinge thickness 226.

In addition to plastic or metal injection molding or cutting of plastic or metal by machining methods, including metal cutting by wire EDM, the first flexible hinge 216 and the second flexible hinge 218 permit exploitation of a planar photo-lithographic metal alloy plating process by orienting the flexible hinges in the plane of the plated layers to enable unitary structures of 1 mm diameter or smaller. Thus the invention enables manufacture of a functional medical instrument jaw of unprecedented smaller size and further enables surgery on correspondingly smaller anatomy such as re-anastomosis of small blood vessels and nerves or manipulation and repair of structures inside the eye.

The first jaw portion 202 can be flexibly integral with the connector portion 206 through the first flexible hinge 216. The second jaw portion 208 can also be flexibly integral with the connector portion 206 through the second flexible hinge 218.

For illustrative purposes, the first flexible hinge 216 and the second flexible hinge 218 have been shown as having the same shape and dimensions, and having a uniform thickness. However, it is understood that the two hinges can be different. For example, the two hinges can have different shapes, dimensions, or a combination thereof and the hinge thickness 226 can vary along the hinge length 224, along a direction perpendicular to the hinge length 224, or both. It is also understood that in an alternate embodiment one jaw portion could be stationary while the other has the reciprocating motion for gripping objects.

The first jaw portion 202 and the second jaw portion 208 can have an adaptor 220 for fastening a task adaptor 222 for specific tasks. The adaptor 220 is a hole or a fastening mechanism for attaching the task adaptor. For example, the adaptor 220 can be a hole or a mechanical fastener for accommodating, such as by fitting or fastening, the task adaptor 222 to the first jaw portion 202, the second jaw portion 208, or a combination thereof.

The task adaptor 222 can be a pad or mechanism for adapting the unitary jaw structure 110 for special tasks. For example, the task adaptor 222 can be a serrated pad for non-slip gripping or a pad with a semi-circular indentation for encircling and grabbing cylindrical objects, such as blood vessels.

Further, it is understood that the first jaw portion 202 and the second jaw portion 208 can be different. For example, the first jaw portion 202 and the second jaw portion 208 can be different from each other in shape. Also, for example, the first jaw portion 202 can be rectangular in shape with the first transverse dimension 210 constant throughout the first jaw portion 202 to provide a broader clamping surface.

The actuator portion 204 is the portion of the unitary jaw structure 110 that causes the reciprocating motion of one or both jaw portions. The actuator portion 204 can be a solid member, such as a bar or wire, that can be moved.

The actuator portion 204 can have rod or a column portion. One of the actuating members 114 of FIG. 1 can be connected or coupled to the rod or the column portion of the actuator portion 204, either without a wrist mechanism or through the wrist mechanism 124 of FIG. 1, to move the actuator portion 204 relative to the connector portion 206.

For example, pulling one of the actuating members 114 at the proximal end 102 of the medical instrument 100 can cause the first jaw portion 202 and the second jaw portion 208 to close. The release of the actuating members 114 where there is no pull or push forces on them can cause the unitary jaw structure 110 to open to a position where the first flexible hinge 216 and the second flexible hinge 218 are straight. Similarly, a push force may be applied to the actuator portion 204 through the actuating members 114 to force one or both jaw portions to open more fully if desired.

In alternative embodiment, the actuator portion 204 can be coupled only to the first jaw portion 202 so that the movement of the actuator portion 204 can cause rotating movement of only the first jaw portion 202.

The hinge portions can be resilient. Therefore, the release of the actuating members 114 where there is no pull or push force on the actuator portion 204 can cause the first jaw portion 202, the second jaw portion 208, or both to move to a position where the first flexible hinge 216 and the second flexible hinge 218 are at a defined neutral position, such as substantially parallel to one another.

The connector portion 206 can be connected to the distal part of the wrist mechanism 124 that is in turn connected to the tube 112. The connector portion 206 can also be directly connect to the tube 112 or can be coupled by an alternative structure.

In one aspect, the first flexible hinge 216 and the second flexible hinge 218 are low equivalent friction structures, such as resilient structures, for allowing movement of the first jaw portion 202 and the second jaw portion 208 relative to the connector portion 206.

In an alternative embodiment, the first flexible hinge 216 and the second flexible hinge 218 can be the compact flexure hinges with all the attendant advantages. The section line 3-3 shows the location and direction of view of the cross-section of FIG. 3 below.

Figure 3:
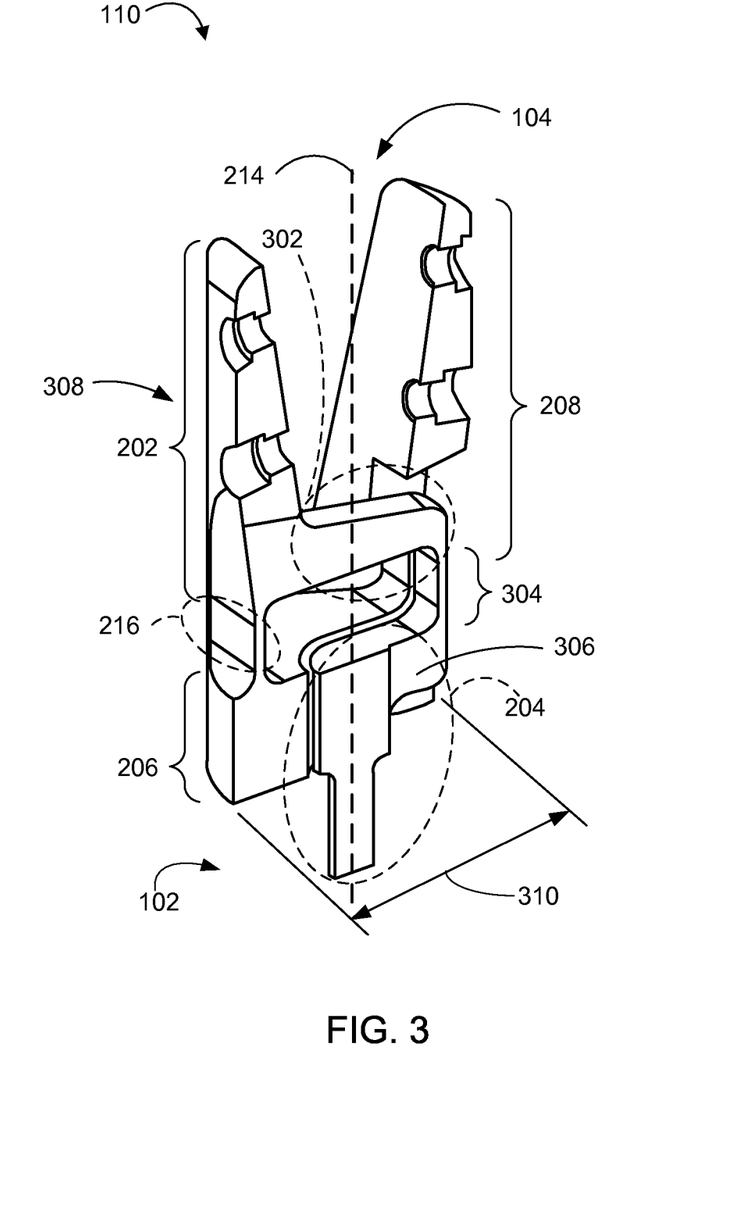
FIG. 3 is a detailed cut-away isometric view of the unitary jaw structure.

Referring now to FIG. 3, therein is shown a detailed cut-away isometric view of the unitary jaw structure 110. The unitary jaw structure 110 can include a flexible jaw mechanism 308 at the distal end 104 and the connector portion 206 at the proximal end 102. The flexible jaw mechanism 308 comprises the first jaw portion 202, the second jaw portion 208, and the actuator portion 204. The flexible jaw mechanism 308 includes a first arm portion 302 and a first arm hinge portion 304 integral with the first jaw portion 202 and the actuator portion 204 respectively. The actuator portion 204 can also have a transverse beam portion 306 perpendicularly connected to the rod or column portion and also coupled to the first jaw portion 202, the second jaw portion 208, or a combination thereof.

Where the second jaw portion 208 is movable, it would similarly have a second arm portion and a second arm hinge portion integral with the second jaw portion 208 and the actuator portion 204 respectively.

One end of the first arm portion 302 extends outwardly from the centerline line 214 to the outer periphery of the second jaw portion 208 and the other end of the first arm portion 302 is integral with the first jaw portion 202 at the first flexible hinge 216. This maximizes the length of the first arm portion 302 to maximize the mechanical advantage for moving the first jaw portion 202. It is understood that the maximum length of the first arm portion 302 is limited by a width 310, which is measured edge to edge along the second transverse dimension 212 of the connector portion 206, of the unitary jaw structure 110. In the event the unitary jaw structure 110 has a circular cross-section, the width 310 would be a diameter 310 of the circular cross-section. As an example, the ratio of the length of the first arm portion 302 from the first flexible hinge 216 to the first arm hinge portion 304 compared to the length of the first jaw portion 202 can be approximately twice as large as the ratio for a design in which a jaw is pivoted on a hinge pin intersecting the center line 214 of a jaw assembly.

It has been discovered that the arrangement of the first arm portion 302, the first flexible hinge 216, and the first arm hinge portion 304 when compared to the length of the first jaw portion 202 provides higher mechanical advantage and lower effective compliance of the actuating members 114 of FIG. 1 viewed from the jaw, thus reducing hysteresis in the motion of the jaw. This hysteresis reduction combines with the improvement gained by the low equivalent friction of the flexible hinges compared with a conventional pin joint hinge.

The first arm hinge portion 304 is a flexure or a flexible member that couples two other relatively rigid members. The first arm hinge portion 304 can be similar to the first flexible hinge 216, the second flexible hinge 218, or a combination thereof. For example, the dimensions, such as the length, and the thickness, can be optimized similar to the first and second flexible hinges. Also, for example, the first arm hinge portion 304 can be a compact flexure hinge. The first arm hinge portion 304 can couple the transverse beam portion 306 of the actuator portion 204 and the first arm portion 302.

The elimination of pivot pin friction, by the flexible jaw mechanism 308, can reduce hysteresis and increase the maximum applicable force at the first jaw portion 202 and the second jaw portion 208. The overall size of the unitary jaw structure 110 can decrease with less reduction of grip force. The resulting decrease in size can provide improved accessibility into smaller and tighter spaces through smaller incisions, which can reduce patient trauma due to the less invasive procedure.

The medical instrument 100 can have the connector portion 206 of the unitary jaw structure 110 coupled to the tube 112 of FIG. 1. The connector portion 206 and the tube 112 can be connected directly or coupled indirectly through the wrist mechanism 124 of FIG. 1. The medical instrument 100 can move the wrist mechanism 124, the tube 112, or a combination thereof to position and orient the connector portion 206 and thereby the unitary jaw structure 110. The tube 112 can hold the connector portion 206 stationary relative to the motion of the actuator portion 204.

Figure 4:
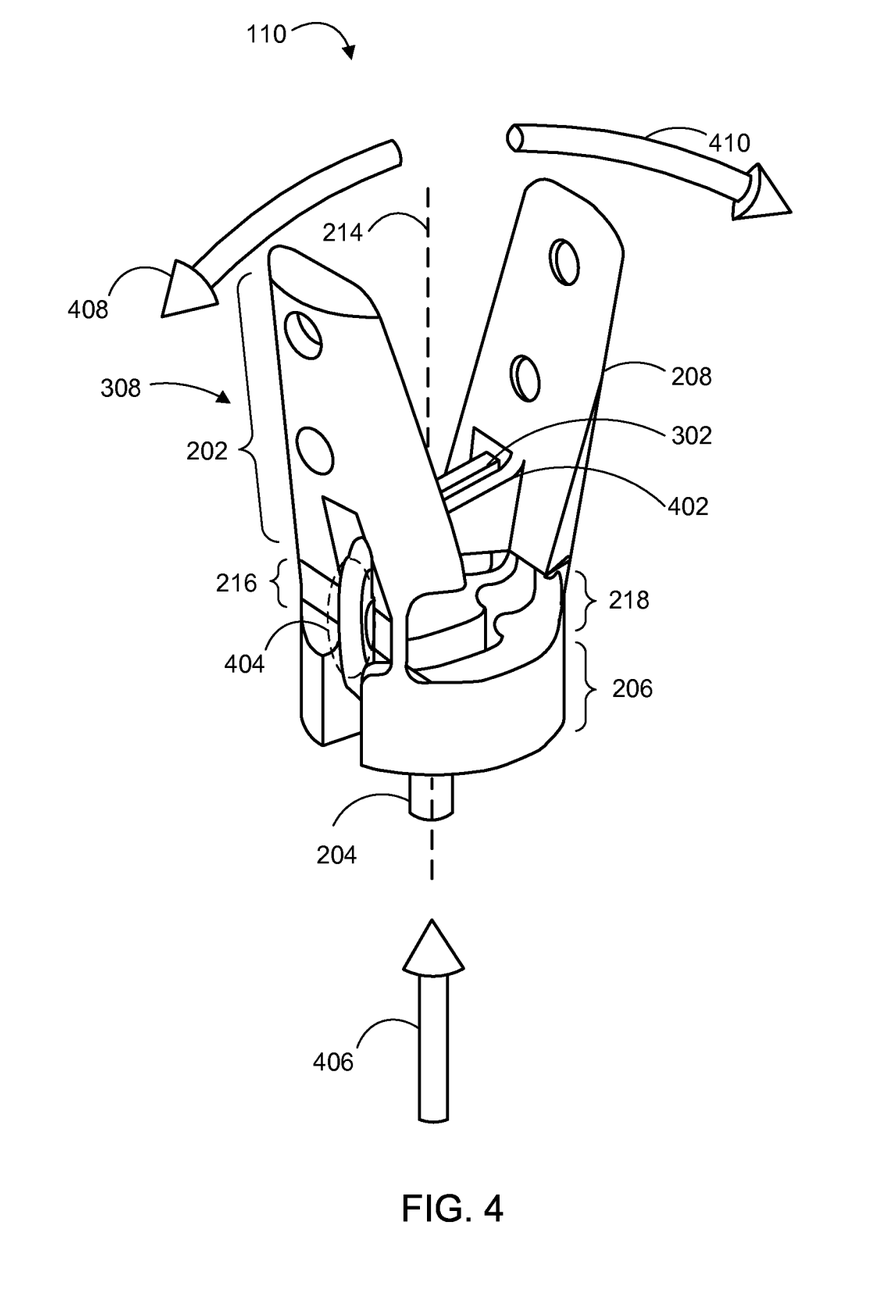
FIG. 4 is an exemplary view of the unitary jaw structure opening.

Referring now to FIG. 4, therein is shown an exemplary view of the unitary jaw structure 110 opening. The second jaw portion 208 is integral with a second arm portion 402 that is integral with a second arm hinge portion 404 that is integral with the actuator portion 204. The shape of the second arm portion 402 can be similar to the first arm portion 302. The shape of the second arm hinge portion 404 can also be similar to the first arm hinge portion 304 of FIG. 3.

The second arm portion 402 can engage the actuator portion 204 at an opposite location from where the first arm portion 302 engages the actuator portion 204.

The actuator portion 204 can be moved upward in a direction 406 to cause the first jaw portion 202 to have an outward movement 408 and the second jaw portion 208 to have an outward movement 410 for an opening of the flexible jaw mechanism 308 of the unitary jaw structure 110. The first jaw portion 202 moves in an arc around the first flexible hinge 216 and the second jaw portion 208 moves in an arc around the second flexible hinge 218. For this movement, the actuator portion 204 would be connected to or part of a rod that is one of the actuating members 114 of FIG. 1, which may be a rod or other component capable of exerting a pushing force, such as a Bowden cable.

Figure 5:
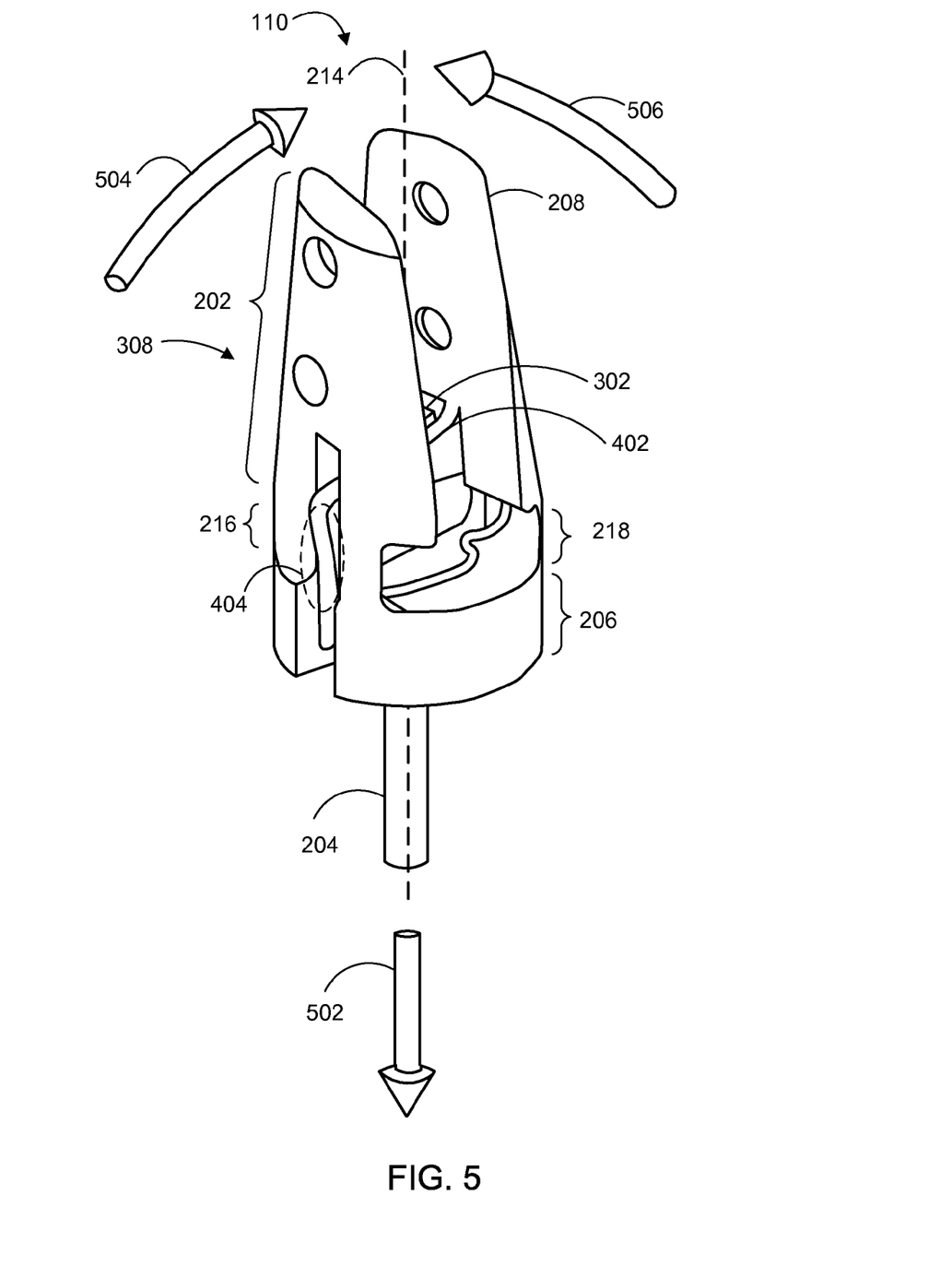
FIG. 5 is an exemplary view of the unitary jaw structure closing.

Referring now to FIG. 5, therein is shown an exemplary view of the unitary jaw structure 110 closing. The actuator portion 204 can be moved downward in a direction 502 to cause the first jaw portion 202 to have an inward movement 504 and the second jaw portion 208 to have an inward movement 506 for a closing of the flexible jaw mechanism 308 of the unitary jaw structure 110. The first jaw portion 202 moves in an arc around the first flexible hinge 216 and the second jaw portion 208 moves in an arc around the second flexible hinge 218. For this movement, the actuator portion 204 would be connected to or part of a rod that is one of the actuating members 114 of FIG. 1. Since there is only a pulling motion involved, the actuator portion 204 could be connected to a wire or cable that is one of the actuating members 114.

The resilient coupling of the first jaw portion 202 and the second jaw portion 208 by the first arm hinge portion 304 of FIG. 3 and the second arm hinge portion 404 of FIGS. 4 and 5, respectively, to the actuator portion 204 and the resilient coupling of the first jaw portion 202 and the second jaw portion 208 by the first flexible hinges 216 and the second flexible hinges 218 to the connector portion 206 can cause the inward movement 504 and the inward movement 506 if the flexible jaw mechanism 308 is open as in FIG. 4 and no force is applied to the actuator portion 204.

The mechanical spring bias, a mechanical property of the first arm hinge portion 304, to straighten at the first arm hinge portion 304 and the second arm hinge portion 404, for example, applies a bias force that causes the first jaw portion 202 and the second jaw portion 208 to close with the inward movement 504 and the inward movement 506 toward the configuration of FIG. 2.

The movement of the actuator portion 204 up and down with vertical reciprocating motion causes rotating reciprocating movement of the first jaw portion 202 and of the second jaw portion 208 about the first flexible hinges 216 and the second flexible hinges 218, respectively.

In summary, the first jaw portion 202 and the second jaw portion 208 of the flexible jaw mechanism 308 are mounted respectively on the first flexible hinge 216 and the second flexible hinge 218 which are offset to the same side of the center line 214 as each respective jaw portion rather than being pivoted on a shaft or pin intersecting the center line 214 as is done throughout the surgical instrument industry today.

In addition, the first flexible hinges 216 and the second flexible hinges 218 for each respective of the first jaw portion 202 and the second jaw portion 208 are located as far as practical off the center line 214 while the jaw portion actuating force is applied to the distal end of the first arm portion 302 and the second arm portion 402, integral with the respective of the first jaw portion 202 and the second jaw portion 208, and extending as far as practical to the opposite side of the center line 214. Additionally, the first arm hinge portion 304 and the second arm hinge portion 404 connect the first arm portion 302 and the second arm portion 402 to a common transverse beam of the actuator portion 204, which is actuated by one of the actuating members 114 fastened to the actuator portion 204 at the beam midpoint on or near the center line 214. Thus, the actuator portion 204 actuates both of the first jaw portion 202 and the second jaw portion 208 equally toward or away from each other.

The first flexible hinges 216 and the second flexible hinges 218 largely eliminate the jaw pivot pin friction torques. The effective axial stiffness for jaw motions of the actuating members 114 connected to the actuator portion 204 is greatly increased by the longer lever arm. The combined effect is to greatly reduce hysteresis manifested as lost or unpredictable motion in the unitary jaw structure 110.

It has been discovered that the first flexible hinges 216 and the second flexible hinges 218 positioned at the outer periphery of the connector portion 206 provide for longer lever arms, which reduce hysteresis that otherwise would have been manifested as lost or unpredictable motion in the unitary jaw structure 110. The reduction of friction by the flexure hinges, such as the first flexible hinges 216 and the second flexible hinges 218, enables jaw grip force sensing at a location proximal to the unitary jaw structure 110 and the tube 112 of FIG. 1. As an example, jaw force in a low friction flexure based jaw mechanism may be sensed where the actuator system 118 applies forces to the actuating member 114 which is connected to the actuator portion 204 rather than on the first jaw portion 202 and the second jaw portion 208, which has practical difficulties. In another aspect, in a low friction jaw mechanism, jaw force sensing may be based on for example, electrical current applied to a motor or pressure applied to a hydraulic or pneumatic actuator.

It has further been discovered that the first arm hinge portion 304 and the second arm hinge portion 404 also reduce hysteresis that otherwise would have been manifested as lost or unpredictable motion in the unitary jaw structure 110, which allows for the jaw force in a low friction flexure based on jaw mechanism to be sensed at the actuator portion 204 and the actuator system 118. The method of sensing at the actuator portion 204 can be similar to the methods described above for the first flexible hinges 216 and the second flexible hinges 218.

It has further yet been discovered that the first arm hinge portion 304 and the second arm hinge portion 404, which operate in tension as well as flexing to close the first jaw portion 202 and the second jaw portion 208 can be designed to limit the maximum applicable jaw force without extra sensing mechanisms. For example, the cross section area of the first arm hinge portion 304 and the second arm hinge portion 404, can be chosen based on a material with a non-linear stress-strain relation such as Nitinol such that the member will transfer only up to a threshold amount of force and deform by lengthening without increase in force when the applied force reaches the threshold maximum based on the stress-strain plateau of that alloy.

The compact flexure hinges 216, of FIG. 2, are designed to provide substantially equal shear and S-bending displacement or shear dominated displacement when a transverse force is applied to the compact flexure, as occurs in reaction to forces applied by the jaws 202 and 208 or the task adaptors 222 to patient tissue or suture needles or the like. A characteristic of the compact flexure hinges 216, when subjected to a transverse force, is that the deflection due to an S-bend component is not more than two times the shear displacement caused by the transverse force.

Embodiments of the present invention have been found to reduce the number of parts in the flexible jaw mechanism 308 from six pieces in some larger discrete component jaw mechanisms or eleven pieces in some smaller discrete component jaw mechanisms to a single integrated part that can be fabricated in a few steps of machining, such as electrical discharge machining or other practical subtractive manufacturing processes.

It has been found that the flexible jaw mechanism 308 can also be fabricated as a single piece by additive processes such as injection molding from plastic or fiber reinforced plastic composite, metal injection molding followed by sintering or by planar photo-lithographic metal plating thus reducing the part cost and the assembly time. The jaw portion flexible hinge may be made of an alloy permitting high strains such as a hardened stainless steel, titanium or aluminum alloy or from Nitinol or other more advanced shape memory alloy with even higher permissible strains or from metallic glass materials.

The working surface of each jaw portion, depending on the application, may be the parent jaw material or the task adaptor 222 of FIG. 2 made of a higher hardness alloy, tungsten carbide, toughened ceramic or finally, a suitable adhered coating such as metal plating, bonded hard grit or other deposit.

The resulting method, process, apparatus, device, product, and/or system is straightforward, cost-effective, uncomplicated, highly versatile, accurate, sensitive, and effective, and can be implemented by adapting known materials and processes for ready, efficient, and economical manufacturing, application, and utilization.

Another important aspect of the present invention is that it valuably supports and services the historical trend of reducing costs, simplifying systems, and increasing performance.

These and other valuable aspects of the present invention consequently further the state of the technology to at least the next level.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters hithertofore set forth herein or shown in the accompanying drawings are to be interpreted in an illustrative and non-limiting sense.

What is claimed is:

1. A medical instrument comprising:
   a unitary jaw structure having:
      a connector portion,
      a first jaw portion flexibly integral with the connector portion,
      a second jaw portion integral with the connector portion,
      a first arm portion integral with the first jaw portion, and
      an actuator portion flexibly integral with the first arm portion for causing rotating motion of the first jaw portion upon linear motion of the actuator portion,
      wherein the connector portion, the first jaw portion, the second jaw portion, the first arm portion, and the actuator portion are all formed in a single piece.

2. The instrument as claimed in claim 1 wherein the unitary jaw structure includes compact flexure hinges formed into the single piece.

3. The instrument as claimed in claim 1 wherein:
   the connector portion has a width and the first jaw portion is flexibly integral with the connector portion at one side of the width;
   the first arm portion extends from the first jaw portion to the other side of the width; and
   the actuator portion is at the center of the width.

4. The instrument as claimed in claim 1 wherein the first jaw portion includes an adaptor for accommodating a task adaptor of different shapes and different materials for different uses of the unitary jaw structure.

5. The instrument as claimed in claim 1,
   the second jaw portion being flexibly integral with the connector portion;
   the unitary jaw structure further including a second arm portion flexibly integral with the second jaw portion and the actuator portion for causing rotating motion of the second jaw portion upon the linear motion of the actuator portion;
   the second arm portion being formed integrally in the single piece with the connector portion, the first jaw portion, the second jaw portion, the first arm portion, and the actuator portion.

6. The instrument as claimed in claim 1 wherein the unitary jaw structure has a taper shape narrower at a distal end.

7. The instrument as claimed in claim 1 wherein the unitary jaw structure has a cylindrical configuration.

8. The instrument as claimed in claim 1 wherein the unitary jaw structure is made of a moldable, shapeable, or joinable plastic or metal.

9. The instrument as claimed in claim 1 further comprising a wrist mechanism connected to the connector portion for orienting the unitary jaw structure.

10. The instrument as claimed in claim 1 further comprising:
- a tube connected directly to the connector portion for holding the connector portion stationary relative to the motion of the actuator portion; and
- actuating members coupled to the actuator portion for causing reciprocating motion of the actuator portion.

11. A medical instrument comprising:
a unitary jaw structure having:
- a connector portion,
- a first flexible hinge integral with the connector portion,
- a first jaw portion integral with the first flexible hinge,
- a second jaw portion integral with the connector portion,
- a first arm portion integral with the first jaw portion,
- a first arm hinge portion integral with the first arm portion, and
- an actuator portion integral with the first arm hinge portion for causing rotating motion of the first jaw portion upon linear motion of the actuator portion,
- wherein the connector portion, the first flexible hinge, the first jaw portion, the second jaw portion, the first arm portion, the first arm hinge, and the actuator portion are all formed in a single piece.

12. The instrument as claimed in claim 11 wherein the unitary jaw structure includes substantially zero friction from the first flexible hinge or the first arm hinge portion.

13. The instrument as claimed in claim 11 wherein:
- the connector portion has a diameter and the first flexible hinge is at one side of the diameter;
- the first arm portion extends from the first jaw portion to the other side of the diameter; and
- the actuator portion is at the center of the diameter.

14. The instrument as claimed in claim 11 wherein the first jaw portion includes an adaptor for accommodating a task adaptor of different shapes and different materials for different applications of the unitary jaw structure.

15. The instrument as claimed in claim 11 wherein the first arm hinge portion, the first arm portion, the first flexible hinge, or a combination thereof is for limiting the force applied at the first jaw portion.

16. The instrument as claimed in claim 11 wherein the unitary jaw structure has a taper shape narrower at a distal end and having rounded corners on the distal end of the first jaw portion.

17. The instrument as claimed in claim 11 wherein the unitary jaw structure has a cylindrical configuration with the first jaw portion having a rounded outer surface.

18. The instrument as claimed in claim 11 wherein the unitary jaw structure is made of:
- a moldable plastic or metal;
- a joinable plastic or metal capable of being joined with other plastics or metals by hot air, heat, or laser welding; or
- a metal shapeable by electrical discharge machining.

19. The instrument as claimed in claim 11 wherein the unitary jaw structure is integral with a wrist mechanism for positioning the unitary jaw structure.

20. The instrument as claimed in claim 11 further comprising:
- a tube having a hollow shape connected directly to the connector portion for holding the connector portion stationary relative to the motion of the actuator portion;
- actuating members encased in the tube and connected to the actuator portion for transferring forces to cause motion of the actuator portion; and
- an actuator system connected to the actuating members for causing reciprocating motion of the actuator portion.

21. A surgical instrument comprising:
- a connector portion, a centerline being defined for the connector portion, a distal direction being defined in one direction along the centerline, a proximal direction being defined opposite the distal direction;
- a first jaw extending in the distal direction from the connector portion at a first side of the connector portion;
- a second jaw extending in the distal direction from the connector portion at a second side of the connector portion, the second side being opposite the first side;
- an actuator portion extending in the proximal direction;
- a first arm extending from the first jaw to join the actuator portion at the second side of the connector portion;
- a second arm extending from the second jaw to join the actuator portion at the first side of the connector portion;
- the connector portion, the first jaw, the second jaw, the actuator portion, the first arm, and the second arm being formed together as a single piece.

22. The surgical instrument of claim 21:
the first jaw being connected to the connector portion at a first flexible hinge;
the second jaw being connected to the connector portion at a second flexible hinge.

23. The surgical instrument of claim 21:
the first arm being connected to the actuator portion at a first flexible hinge at the second side of the connector portion;
the second arm being connected to the actuator portion at a second flexible hinge at the first side of the connector portion.

* * * * *